(12) United States Patent
VanSkiver et al.

(10) Patent No.: US 6,660,029 B2
(45) Date of Patent: Dec. 9, 2003

(54) HINGED THERAPEUTIC MOUTHPIECE

(76) Inventors: Greg J. VanSkiver, 1514 Heritage Dr., Hastings, NE (US) 68901; Roxanne R. VanSkiver, 1514 Heritage Dr., Hastings, NE (US) 68901

( * ) Notice: Subject to any disclaimer, the term of this patent is extended or adjusted under 35 U.S.C. 154(b) by 0 days.

(21) Appl. No.: 10/209,310

(22) Filed: Jul. 31, 2002

(65) Prior Publication Data

US 2003/0055474 A1 Mar. 20, 2003

Related U.S. Application Data

(60) Provisional application No. 60/309,327, filed on Aug. 1, 2001.

(51) Int. Cl.⁷ .................................................. A61F 7/12
(52) U.S. Cl. ........................ 607/113; 607/96; 607/112
(58) Field of Search ...................... 607/96–113; 606/70, 606/21, 27; 433/37, 38

(56) References Cited

U.S. PATENT DOCUMENTS

| | | | |
|---|---|---|---|
| 3,885,403 A | | 5/1975 | Spencer |
| 4,440,167 A | * | 4/1984 | Takehisa ..................... 606/20 |
| 4,982,122 A | | 1/1991 | Rowe et al. |
| 4,983,122 A | * | 1/1991 | Mitnick ...................... 607/105 |
| 5,323,787 A | * | 6/1994 | Pratt .......................... 128/862 |
| 5,494,441 A | * | 2/1996 | Nicholson .................... 433/215 |
| 5,509,801 A | * | 4/1996 | Nicholson .................... 601/139 |
| 5,515,870 A | | 5/1996 | Zilber |
| 5,520,016 A | | 5/1996 | Liu |
| 5,551,952 A | | 9/1996 | Falgout |
| 5,606,871 A | | 3/1997 | Hansen et al. |
| 5,649,964 A | | 7/1997 | Berman et al. |
| 5,653,731 A | | 8/1997 | Rohrig |
| 5,666,693 A | | 9/1997 | Levay |
| 5,782,868 A | | 7/1998 | Moore, Jr. |
| 5,819,144 A | | 10/1998 | Okada et al. |
| 5,902,322 A | | 5/1999 | Scagliotti |

* cited by examiner

*Primary Examiner*—Roy D. Gibson
*Assistant Examiner*—Henry M. Johnson
(74) *Attorney, Agent, or Firm*—Knobbe Martens Olson & Bear LLP

(57) ABSTRACT

This invention relates to devices for insertion into the mouth for the application of heat or cold to oral tissue to provide a therapeutic effect. The device 10 includes an upper member 11 substantially conforming to a contour of an upper gum line, a lower member 12 substantially conforming to a contour of a lower gum line, a first hinge member 13, and a second hinge member 14, wherein at least one hinge member 13, 14 is configured to exert a compressive force to maintain the upper member 11 substantially in contact with an upper gum and the lower member 12 substantially in contact with a lower gum.

20 Claims, 3 Drawing Sheets

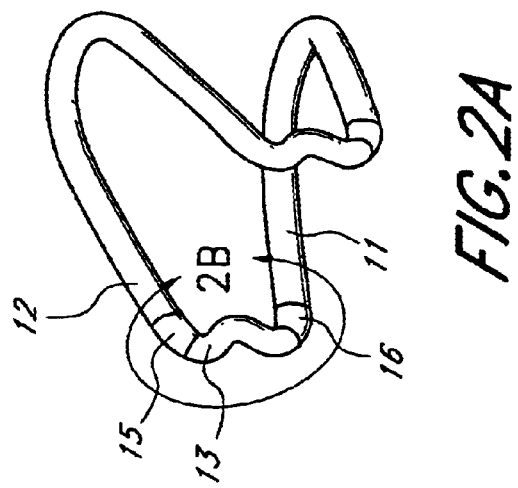
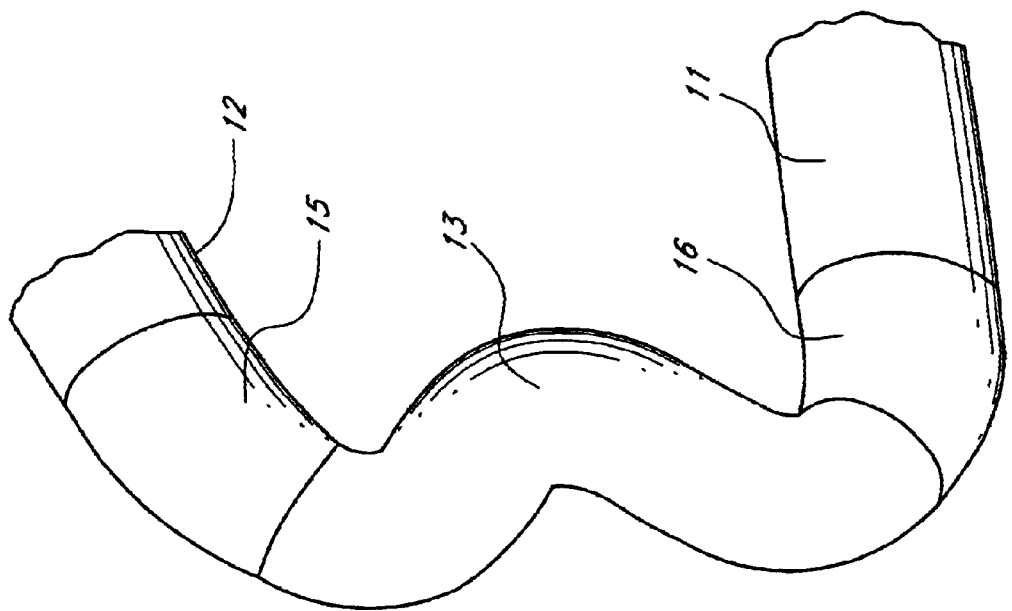

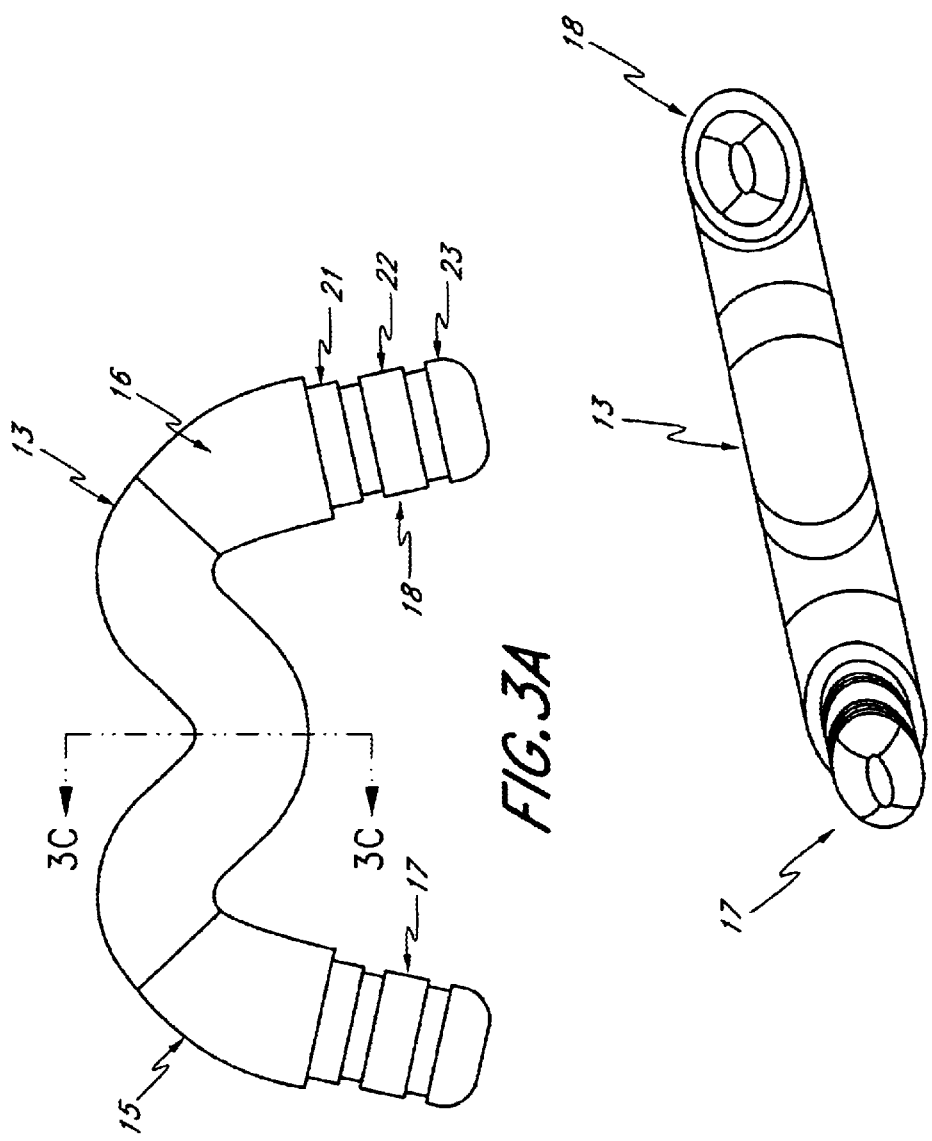

HINGED THERAPEUTIC MOUTHPIECE

RELATED APPLICATION

This application claims the benefit of U.S. Provisional Application No. 60/309,327, filed Aug. 1, 2001.

FIELD OF THE INVENTION

This invention relates to devices for insertion into the mouth for the application of heat or cold to oral tissue to provide a therapeutic effect.

BACKGROUND OF THE INVENTION

Cryoanesthesia, or the localized application of cold as a means of producing regional anesthesia, for non-parenteral relief of pain is an accepted method for treating oral tissue. The basic physiologic effects of cooling tissue may include decreased local metabolism, vasoconstriction, reduced swelling, decreased hemorrhage, and analgesia. The magnitude and/or type of the effect generally depends upon the application method and duration of the treatment. Cryoanesthesia or cryotherapy may be preferred for a variety of indications, including decreasing swelling or bleeding after oral surgery, to treat burns, to reduce inflammation due to allergic reaction, or to reduce pain. Conventionally, cryoanesthesia or cryotherapy involves external application of ice or cold packs to the jaw or face.

Likewise, heat therapy or thermal treatments may be useful for certain conditions of the oral tissue. For example, application of heat may relieve painful muscle spasms or cramping, or the pain of temporomandibular joint disease or headache. As with cryotherapy, heat therapy conventionally involves application of a hot pack or heating pad to the skin of the jaw or face. The conventional methods of applying heat or cold to oral tissue suffer the drawback that the heat or cold must be conducted through the skin and underlying tissue to the oral tissue to be treated.

SUMMARY OF THE INVENTION

There is a need for a device and method for effectively and efficiently providing anesthesia or pain relief to the oral tissue. Specifically, a device and method that may be used to apply heat or cold directly to a localized area of the oral tissue may be especially desirable.

One aspect of the present invention includes the realization that oral thermal therapy can be more effective and efficient if the device is placed in direct contact with oral tissue that is the subject of therapy. Indirect application of heat or cold to oral tissue is less efficient because the thermal energy is conducted through facial skin and the underlying tissue, thereby attenuating the flow of thermal energy into and out of the oral tissue to be treated. Thus, by directly applying heat or cold to a localized area of oral tissue, anesthetic and other effects can be achieved more effectively and efficiently.

The preferred embodiments of the present invention facilitate the application of cold to the gums, which may be especially helpful to reduce pain and swelling before, during, and after dental or other procedures, and for alleviating pain associated with trauma to the oral cavity. The application of cold may also provide relief from mouth sores and headaches, and may be helpful in pretreatment for certain procedures. The device of preferred embodiments may offer a significant advantage over ice cubes, cold drinks, and the like, because it localizes the cold to the gums or oral tissue without affecting the teeth. It is beneficial to avoid contact with the teeth since they are often sensitive to cold. The invention also has the advantages of being reusable and minimally invasive.

One preferred embodiment is a device that can be positioned between the gum line and the inner wall of the cheek. In one aspect of a preferred embodiment, two tube-like, flexible elements are curved in a semicircular shape or other shape similar to the curve of a patient's gum line. These semicircular elements are preferably connected to each other by two bendable hinge members. The bendable hinge members may be integral with the semicircular elements, or may be removably attached to the semicircular elements by an appropriate joint configuration.

When worn within the mouth, one semicircular element contacts the upper gum, one semicircular element contacts the lower gum, and the hinge members are positioned toward the back of the mouth. The thickness of the semicircular elements is preferably selected such that they extend over the gum area, while minimizing contact with the teeth. The hinge members allow the device to deform slightly when a gently squeezing pressure is applied. Compressing the device in this way facilitates positioning the device in the mouth. The hinge members are also slightly compressed during normal use, and the pressure exerted in opposition to the compression force helps the device remain in position within the mouth. The hinge members preferably operate in a manner that does not risk trauma to the gum or cheek area.

In one preferred embodiment of the invention, the semicircular elements are hollow and are filled with a non-toxic solution that, when cooled, still remains flexible. In an alternative embodiment, the semicircular elements are solid and composed of a material that is capable of retaining cold or heat without the aid of an encapsulated substance. In other embodiments, a spongy material capable of retaining a cooling or heating material is utilized. In each embodiment, the semicircular elements are preferably soft for comfort yet durable so as to avoid compromising the device if it is accidentally bitten or used in conjunction with braces, dentures, or other oral or medical devices or procedures.

BRIEF DESCRIPTION OF THE DRAWINGS

FIG. 1b provides a top plan view of the device of FIG. 1a.

FIG. 1c provides a rear elevational view of the device of FIG. 1a.

FIG. 2a provides a rear, top, and right side perspective view of a device of a preferred embodiment.

FIG. 2b provides an enlarged view of a portion of the device identified by a circle in FIG. 2a.

FIG. 3a provides a plan view of a device of a preferred embodiment.

FIG. 3b provides a front elevational view of the device of FIG. 3a.

FIG. 3c provides a sectional view taken along line 3a—3a of FIG. 3a.

DETAILED DESCRIPTION OF THE PREFERRED EMBODIMENTS

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Devices for use in the oral cavity to provide soothing or pain relief are described in the patent literature, for example, U.S. Pat. No. 5,819,144 "Therapeutic mouthpiece"; U.S. Pat. No. 4,983,122 "Dental compress"; U.S. Pat. No. 5,323,787 "Custom fitted mouthpiece w/medicated pad and container"; U.S. Pat. No. 3,885,403 "Hot and cold compress"; U.S. Pat. No. 5,782,868 "Gel filled teething device"; U.S. Pat. No. 5,606,871 "Pacifier shaped teether with cold storage container"; U.S. Pat. No. D420,447 "Teething ring"; U.S. Pat. No. D411,303 "Vibrating teething ring"; U.S. Pat. No. 5,902,322 "Vibrating teething ring"; U.S. Pat. No. 5,766,223 "Child's teething device"; U.S. Pat. No. D391,363 "Teething ring"; U.S. Pat. No. 5,666,693 "Toy handle for oral device"; U.S. Pat. No. 5,653,731 "Pacifier having a shield with chewing beads"; U.S. Pat. No. 5,649,964 "Vibrating teething ring device"; U.S. Pat. No. 5,606,871 "Pacifier shaped teether with cold storage container"; U.S. Pat. No. 5,551,952 "Teething ring"; U.S. Pat. No. 5,520,016 "Ring and catch and method"; and U.S. Pat. No. 5,515,870 "Thumb and finger sucking prevention device." Teething rings and other cold compress devices are commercially available, including Doctor's Choice Gum Soother marketed by Danara Intl., Ltd., of North Bergen, N.J.; Playskool Ice Cream Teether marketed by Safety 1$^{st}$, Inc. of Canton Mass.; Cooling Gum Soother marketed by Babies Best, Inc., of Vernon, Calif.; and Certi Cool Instant Cold Compress marketed by Certified Safety Manufacturing, Inc. of Kansas City, Mo. Such devices may have certain drawbacks that make them unsuitable or not preferred for use in certain applications.

In contrast, the devices of the preferred embodiments are useful in a variety of applications, and are particularly effective in administering cryoanesthesia to localized areas of the oral tissue.

Figure 1B:
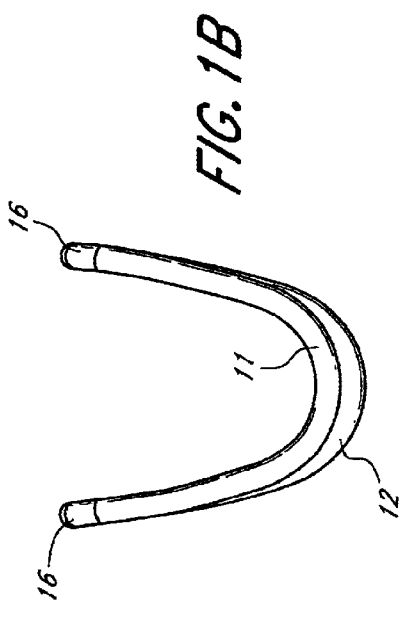
Figure 1E:
FIG. 1e provides an enlarged view of a portion of the device identified by a circle in FIG. 1d.
Figure 1D:
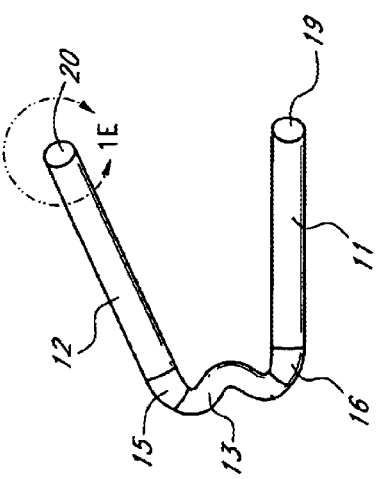
FIG. 1d provides a sectional view taken along line 1c—1c of FIG. 1c.
Figure 1A:
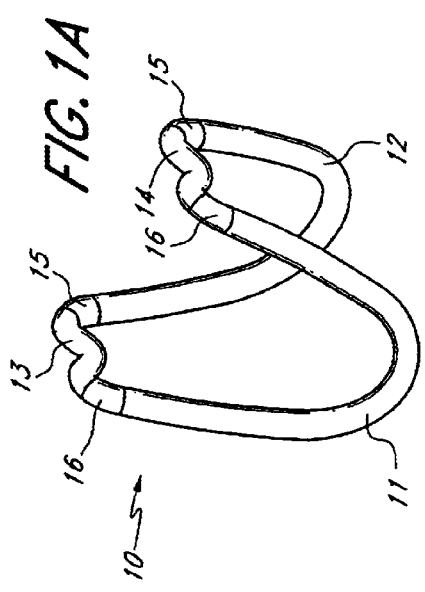
FIG. 1a provides a rear, top, and left side perspective view of a device of a preferred embodiment.
Figure 1C:
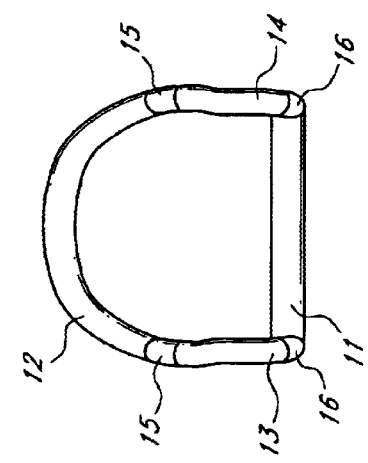

Referring to the FIGS. 1a, 1b, and 1c, a preferred embodiment of a dental device 10 or mouthpiece as shown includes a lower element 11, and an upper element 12 curved to fit along an average gum line. Preferably, the upper and lower elements 11, 12 are rod or tube shaped. The lower element 11 is specially shaped to conform to the lower gum line and the upper element 12 is specially shaped to conform to the upper gum line.

Elements 11, 12 are also preferably capable of deforming sufficiently to comfortably fit different gum lines. The dimensions of elements 11, 12 are such that in an average application, the device maximizes contact with the gums while minimizing contact with the teeth. In various embodiments, the dimensions of the device may be adjusted as desired to fit certain jaw sizes, e.g., children of various ages, adult women, adult men, and the like. Alternatively, if the device is for use in veterinary applications, the dimensions of the elements may be selected so as to provide a proper fit to the gum line of the animal being treated.

As depicted in FIG. 1d, the cross-sectional view along line 1a–1a of FIG. 1c, the elements 11, 12 are hollow and have a relatively thin wall, as depicted in the enlarged view provided in FIG. 1e. Preferably, the elements 11, 12 have a maximum outer diameter of about 3 mm or less to about 20 mm or more, preferably about 4, 5, or 6 mm to about 15, 16, 17, 18, or 19 mm, more preferably about 7, 8, or 9 mm to about 11, 12, 13, or 14 mm, and most preferably about 10 mm.

The preferred maximum outer diameter of elements 11, 12 may vary, depending upon the characteristics and configuration of the oral cavity. Preferably, the thickness of the wall of the elements 11, 12 is less than about 0.5 mm to greater than about 2 mm, preferably about 0.75 mm to about 1.25 to 1.5 mm, most preferably about 1 mm. The preferred thickness may vary, depending upon the material from which the tube is fabricated. Thinner walls may facilitate heat transfer and flexibility of the device, while thicker walls may provide improved structural integrity, durability, and rigidity. While tubing having a circular cross section is generally preferred, tubing having an oval or elliptical cross section, or any other suitable shaped cross section, may also be preferred.

As depicted in FIGS. 1a, 1b, 1c, 1d, and 1e the lower element 11 is connected to the upper element 12 by bendable hinge members 13, 14. The hinge members 13, 14 are configured to maintain a slight downward force on element 11 against the lower gum and a slightly upward force on element 12 against the upper gum when the device 10 is positioned in the oral cavity.

FIG. 2a provides detail for the hinge member depicted in the device of FIG. 2b. In this embodiment, elements 11, 12 are fabricated from oval tubing, while the hinge members 13, 14 are fabricated from tubing having a circular cross section. Sections of tubing 15, 16 provide a transition from the oval tubing of elements 11, 12 to round tubing of the hinge members 13, 14.

The transitions 15, 16, elements 11, 12, and hinge members 13, 14 may be fabricated in any suitable or convenient manner. For example, the different cross section shapes may be imposed on a unitary piece of tubing to form the transition members 15, 16, elements 11, 12, and hinge members 13, 14. Alternatively, two or more sections of tubing or shaped pieces may be affixed or joined together to form transition members 15, 16, elements 11, 12, and hinge members 13, 14.

In a hinge member 13 of one embodiment, depicted in FIGS. 3a–c, transition members 15, 16 are situated on either end of hinge member 13. The transition members 15, 16 are provided with connectors 17, 18 having at least one annular projection 21, 22, 23. The connectors 17, 18 are configured to form a seal with elements 11, 12 upon insertion of the connector 17 or 18 into a lumen at an end of element 11 or 12. Preferably, the maximum diameter of the annular projections 21, 22, 23 is slightly larger than the inner diameter of the elements 11, 12, which are constructed of a flexible material, thereby providing a secure fit after insertion of the connectors 17, 18 into the ends of the elements 11, 12.

In one embodiment, the device 10 is fabricated to have a specific hinge angle. In preferred embodiments, the hinge angle, when no compressive force is applied, may vary from about 5° or less to about 45° or more, preferably about 10° to about 40°, more preferably about 15° to about 35°, and most preferably from about 20° to about 30°.

In preferred embodiments, the device is provided to the practitioner in a ready-to-use form. However, in certain embodiments, it may be desired by the practitioner to adjust the device prior to use. For example, it may be desirable to adjust the hinge angle so as to better conform the device to the shape of a particular patient's mouth, or to adjust the radius of the hinge member to increase or decrease the length of the arch for a comfortable fit. In such embodiments, the hinge members or other components of the device may be fabricated from a material that is pliable upon the application of heat, yet substantially resilient at room temperature. The hinge or other member may then be heated, bent into the desired shape or angle, then cooled to thereby retain its new shape.

In preferred embodiments, the material from which the hinge member is fabricated is preferably pliable yet have some degree of rigidity such that it can be bent into a new shape and substantially retain that new shape in the absence of deforming forces. The material is also preferably sufficiently resilient such that it can accommodate a range of deforming forces, for example, the natural movement of the mouth, without a substantial effect on the device's resting shape (i.e., its shape in the absence of deforming forces). Materials that are pliable at room temperature but which have memory, i.e., materials that substantially return to their original shape after a deforming force is removed, are generally preferred.

In preferred embodiments, the lower and upper elements 11, 12 are slightly compressed when the device is in position in the patient's mouth to maintain snug contact between the gum line and the inner wall of the cheek. In addition to gently holding elements 11, 12 in place, hinge members 13, 14 aid in moving the device into and out of the mouth. In a preferred embodiment, the hinge members 13, 14 and elements 11, 12 are provided with an interlocking click mechanism that permits the length of the arch to be adjusted to fit different jaw sizes. In such a configuration, the hinge member 11 or 12 and element 11 or 12 may be moved apart or together then clicked in place to provide a comfortable fit.

The hinge member is preferably of a "E" shape, as depicted in the Figures. This configuration offers the benefit of improved compression and comfortable fit when the device is in position, especially during jaw movements, e.g., while speaking. However, in other embodiments, different hinge configurations may be preferred. For example, the hinge member may preferably be a simple "C" shape capable of exerting a compressive force. In other embodiments, the hinge member may include a leaf spring, torsional spring, or other spring, optionally in combination with a simple hinge not configured to exert a compressive force.

In preferred embodiments, the materials from which the device is constructed are solid and have a satisfactory capacity for retaining heat or cold for an extended period of time while the device is positioned in the mouth. The device may be cooled in a refrigerator or freezer before it is positioned inside the mouth. Likewise, if application of heat is desired, the material may be heated, e.g., in warm water, a convection heating oven, a microwave oven, or the like, and then maintain its warm temperature for an extended period of time after it is positioned in the mouth. The material preferably is capable of maintaining its flexibility after it is chilled, if it used to cool oral tissue. Likewise, the material preferably is capable of maintaining some degree of rigidity or form after it is heated, if it is to be utilized for warming oral tissue.

In an alternate embodiment, rather than being constructed of solid material, elements 11, 12 are hollow and filled with a liquid or gel that preferably is capable of maintaining its cold temperature (or warm temperature) and flexibility (or rigidity) while in use. This encapsulated substance preferably is non-toxic, in case of accidental leakage.

FIGS. 1d and 1e illustrate a cross section of a device having a configuration characterized by the internal fluid or gel chambers 19, 20 of elements 11, 12. In a preferred embodiment, the encapsulated substance is a two-phase system, for example, glycerol in water. In a particularly preferred embodiment, a 10% glycerol solution in water is employed. Also suitable for use is a 5 wt. % saline (NaCl) solution. Any suitable liquid or gel may be used, however, including but not limited to water, or water in combination with a non-toxic gelling substance.

For ease of fabrication, it is preferred to construct the two tube-like elements 11, 12 from commercially available tubing of an acceptable diameter cut to an appropriate length. Such tubing generally has a circular cross-section. However, in certain embodiments it may be desired to utilize tubing having a different cross-sectional shape, for example, elliptical, semicircular, oval, square, triangular, or irregular shape. Likewise, it may be desired for the cross sectional shape and/or area to vary along the length of the element. For example, it may be desirable to utilize a smaller cross-sectional area and/or a thinner profile in areas adjacent to the lips, and a larger cross-sectional area and/or a thicker profile in areas adjacent to the cheeks. Similarly, the thickness of the wall of the tube may be varied as desired, e.g. to provide a greater or lesser degree of flexibility or to facilitate transfer of heat or cold from the device to the oral tissue.

In certain embodiments, it may be desired to apply heat or cold to a only one region of the mouth, for example, only the upper gums, the lower gums, the area adjacent to the back teeth, the area adjacent to the front teeth, one side of the mouth, a particular tooth or teeth, one or both hinges of the jaw, or the like. In such embodiments, it may be desired to provide a tubular material comprising the tube-like elements 11, 12 or hollow bendable hinge members 13, 14 with one or more septums in the lumen of the member. The septum or septums delineate an area or areas to be filled with a liquid or gel that is capable of maintaining its cold temperature, with the remaining areas encapsulating air or another material of lower heat capacity than the gel or liquid. Alternatively, elements 11, 12, 13, and/or 14 may comprise composite materials. In such embodiments, a portion of a high heat capacity solid polymer or other material may be secured to a portion of lower heat capacity, e.g., a hollow air-filled tube or a polymeric material with lower heat capacity. In a particularly preferred embodiment, one or both of elements 11, 12 may comprise a high heat capacity structure (e.g., a solid or spongy polymeric material or tube containing a cooling or heating gel or liquid), while the hinge members 13, 14 comprise hollow polymeric structures.

In some embodiments, the hinge members 13, 14 do not directly contact the gum line, and thus do not need to stay cold (or warm). By way of specific example, the embodiment depicted in FIG. 1d where elements 11, 12 are hollow, the internal fluid or gel chambers 19, 20 need not extend through the hinge members 13, 14 if cooling of the cooling of the hinge members is not preferred. In other embodiments, the hinge members 13, 14 may be formed integral with elements 11, 12 during the molding of the plastic material.

The devices of the preferred embodiments can be advantageously made from any of a variety of medical grade or biocompatible materials, including ceramics, metals, polymers (such as homopolymers, copolymers, terpolymers, chemically or otherwise modified polymers, cross-linked polymers, coated polymers, resins, mixtures and combinations of polymers and the like), composites, and the like, which are well known to those of skill in the medical device manufacturing arts, including polytetrafluoroethylene (marketed under the tradename TEFLON™, available from E.I. du Pont de Nemours and Company of Wilmington, Del.), various densities of polyethylene, nylon, polyethylethylketone (PEEK), polyethylene terephthalate (PET), polyether block amide copolymer (PEBAX), polymethylmethacrylate (PMMA), polytetrafluoroethylene (PTFE), polyurethane, polyvinylchloride (PVC), polydimethylsiloxane (PDMS), silicones, resin copolymers, and other materials known in the art. In a particularly preferred embodiment, the polymeric material comprises a styrenic copolymer (marketed under the tradename KRATON™, available from Kraton Polymers of Houston, Tex.). Also preferred are silicone elastomers in the 20 to 70 Shore A hardness range, available from GE Silicones. Particularly preferred polymeric materials have a Shore A hardness of about 10 or less to about 80 or more, preferably about 15, 20, 25, or 30 to about 60, 65, 70, 75, 80, or 85, more preferably about 30 or 35 to about 50 or 55, and most preferably about 40 to about 45.

Any of a variety of additional materials may also be used. Suitable manufacturing methods and apparatus are also well known including injection molding and extrusion of the polymers and combination of polymers. Selection of suitable materials can be readily accomplished by those of skill in the art, taking into account the desired physical properties of the finished device, as well as the desired manufacturing process and other product design considerations such as one time use.

Desired temperatures for the therapeutic application of heat or cold generally range from just above body-temperature (+37° C.) for heat-therapy to just above freezing (+0° C.) for cold-therapy. When heat is applied to the oral tissue, the temperature is preferably from about 38° C. to about 49° C., more preferably from about 39, 40, or 41° C. to about 46, 47, or 48° C., and most preferably from about 42 or 43° C. to about 44 or 45° C. When cold is applied to the oral tissue, the temperature is preferably from about 4° C. to about 15° C., more preferably from about 5, 6, 7, or 8° C. to about 11, 12, 13, or 14° C., and most preferably from about 9° C. to about 10° C. While these ranges are typically preferred for the application of cold or heat, respectively, in certain embodiments temperatures outside of these ranges may be preferred.

Heat may be generated within the device by an exothermic reaction or phase change, or may be transferred from a pre-heated mouthpiece to adjacent oral tissue. Likewise, cold may be generated by an endothermic reaction or phase change, or may be transferred to adjacent oral tissue from a pre-cooled mouthpiece.

In certain embodiments, it may be preferred that heating or cooling be provided without the need for increasing or reducing the temperature of the mouthpiece by external means prior to insertion into the mouth. In such embodiments, the mouthpiece is maintained at ambient temperature but yields heat or cold when desired after initiation of a chemical reaction, e.g., by mixing two chemical components maintained in separate compartments in the mouthpiece, e.g., by piercing or otherwise rupturing a septum between the compartments. In other embodiments, it may be preferred to apply heat or cold after the mouthpiece is removed from a cooling or heating device. In such embodiments, a high heat capacity substance or a phase change material is preferably used. An example of a common phase change material is ice, however other materials, such as encapsulated gels as are known in the art may also be used. In other embodiments, it may be preferred to generate heat within the device by non-chemical means, e.g., a resistive heating unit (either battery operated or provided with an external power source) incorporated into the device.

It may be desired to reuse the device after appropriate disinfecting procedures. In such embodiments, the device may be capable of reuse after a regeneration process, such as reheating, recooling, or the like. Alternatively, if the device is adapted to be discarded after a single use, then an irreversible system may be employed, i.e., an endothermic or exothermic chemical reaction between two mixed components.

In a preferred embodiment wherein pre-cooling of the device by external means is not desired, cooling is applied via a sodium-acetate-hydrate phase change system contained within the device. The system comprises a sodium acetate aqueous solution in metastable equilibrium at ambient temperature and pressure, which undergoes a phase change upon addition of seed crystals or a pressure pulse. Pure sodium acetate is a water-soluble food grade salt which forms a hydrate compound with water in an endothermic reaction. The reaction may be reversed by heating.

Heating may be applied by using a heating system comprising water and anhydrous calcium chloride salt. When mixed, an exothermic reaction occurs. Heat may also be generated by an oxidative exothermic process, e.g., oxidation of iron powder to iron oxide in the presence of a water-charcoal-salt-cellulose gel. In preferred embodiments wherein heat is to be applied, a paraffinic material such as hexadecane is used. Such materials provide a more comfortable temperature level than most other systems, and are generally non-toxic.

In certain embodiments, it may be preferred to incorporate a rubber-like polymeric material into the device. The term "rubber-like," as used herein, is a broad term and is used in its ordinary sense, including, without limitation, a polymeric material exhibiting memory. A polymeric material exhibiting memory returns to its original shape when a deforming force is removed. Examples of rubber-like materials include, but are not limited to, chloroprene rubber, neoprene, styrene butadiene rubber, acrylonitrile butadiene rubber, ethylene propylene diene methylene (EPDM), and plastics such as polyvinylchloride and polyethylene that are compounded and cured to impart rubber-like properties.

Such rubber-like materials may be solid or spongy. Spongy materials possess a cellular structure. Spongy materials may generally be divided into two classes: open cell and closed cell. Open-cell sponges possess an interconnected cell structure that permits the absorption and circulation of gases and liquids. The open-cell structure permits the spongy material to absorb and retain a heating or cooling material. Closed cell sponges incorporate a plurality of encapsulated pockets containing air or another gaseous material. Because the pores are not interconnected, absorption of gases and liquids by the material is minimal.

In various embodiments, spongy materials of varying density may be used. For example, if it is desired that the device incorporate an open cell sponge, wherein the sponge absorbs a cooling or heating material, e.g., cool or warm water, prior to insertion into the oral cavity, it may be preferred to utilize a sponge with a low density. Alternatively, if the device contains a closed cell sponge, and the polymeric material of the sponge is pre-cooled or preheated prior to insertion into the oral cavity, a high density sponge may be preferred because of the greater heat capacity of the polymeric material compared to the encapsulated gas.

In another embodiment, the device is configured to permit circulation of a cooling or heating medium at a desired temperature through the device. In such an embodiment, the device preferably incorporates an outer wall enclosing a lumen, wherein the lumen is interrupted at a single point on the cross section of the lumen by a septum, with an ingress and an egress into the luminal space provided on either side of the septum. The cooling or heating medium is supplied to the device via the ingress from a heating or cooling source and removed via the egress. If a high degree of temperature control is desired, the heating or cooling source may incorporate a reservoir containing the cooling or heating medium, a means for heating or cooling the medium, e.g., a resistive heating coil or a cooling jacket, a thermostat, a pump, a supply line connecting the reservoir to the ingress, and a discharge line from the egress back to the reservoir. Alternatively, if a high degree of temperature control is not desired, the ingress may be connected to a supply of warm or cold tap water, and the egress connected to a drain.

In yet another embodiment, the device is configured to permit delivery of a medicament or other desired substance to the tissue adjacent to the device. In such an embodiment, the device preferably incorporates a permeable outer wall enclosing a lumen, wherein the lumen is filled with a medicament or medicament-containing substance. Saliva present in the mouth results in a fluid communication between the lumen and the surrounding oral tissue through passages in the outer wall. This fluid communication permits the delivery of medicament to the surrounding tissue in a controlled fashion.

The rate at which the medicament is delivered may be regulated by adjusting the porosity of the outer wall of the lumen, with a greater degree of porosity correlating with a faster rate of delivery of the medicament. Depending upon the embodiment, the pores in the outer wall may be large or small, or numerous or few. The desired degree and nature of the porosity may vary depending upon the medicament to be delivered, the material of the outer wall, the delivery rate of the medicament, the concentration or amount of diluent in the lumen, and the like. Alternatively, the rate at which the medicament is delivered may be adjusted by providing the medicament in a matrix, which inhibits solubilization, e.g., in a porous sponge, a slow-dissolving solid matrix. The use of a matrix, diluent, or slow release system for the medicament may be preferred in certain embodiments, especially when a liquid medicament is utilized. Alternatively, the device may include a solid permeable substance with no lumen, wherein the medicament is incorporated into pores or passages of the permeable substance, or the medicament is imbedded into the material of a permeable wall.

In certain embodiments, it may be desirable to deliver both a medicament and heat or cooling to the adjacent oral tissue. In such embodiments, the medicament may be imbedded into the wall material and a cooling or heating medium contained in the lumen. Alternatively, the device may include a lumen divided along its length by a septum, with cooling or heating medium contained on one side of the septum, and the medicament on the other side, with the outer wall adjacent to the medicament-containing portion of the lumen provided with passages or pores permitting fluid communication with surrounding oral tissue.

Various combinations of materials or composite materials, e.g., layered materials or laminates, may be utilized, depending upon the desired effect.

It is generally preferred to apply cold to oral tissue using a device of a preferred embodiment for a period of about 1 minute or less to about 20 minutes or longer, preferably about 2, 3, or 4 minutes to about 10 or 15 minutes, most preferably about 5 or 6 minutes to about 7, 8, or 9 minutes. If desired, one or more additional cold treatments may then be applied. It is generally preferred to provide an interval of several minutes to half an hour between treatments, however in certain embodiments no interval or a longer interval may be desirable.

The devices of the various preferred embodiments are suitable for a variety of preoperative and postoperative uses. For example, preoperative uses may include, but are not limited to, the treatment of preexisting pain, swelling, infection, or trauma in the oral cavity. Postoperative uses include treatment of general discomfort following periodontal procedures, orthodontic procedures, endodontic procedures, oral and maxillofacial surgery, and general dentistry.

The devices of preferred embodiments can be useful in the treatment of maxillofacial and orofacial pain; in regional anesthesia applications; in applications involving nerve blocks without collateral numbness; in applications where the patient is endentulous, allergic to epinephrine or other analgesics, or has high blood pressure or heart problems; and in applications where there is failed local anesthesia, pain from implantables, leucocytosis with chronic pain, masticatory muscle hyperfunction, neuropathic pain, peripheral nerve injury, facial neuralgia, temporal mandibular disease, jaw joint pain, painful oral sores, oral mucositis pain, ondotostomatological pain, masticatory muscle pain, root canals, severe toothache, extraction, deep scaling, root planing, and orthognathia and micrognathia with surgical reconstruction. While the devices are particularly preferred for the non-parenteral relief of pain by cryoanesthesia, the devices are also suitable for use in conjunction with conventional anesthetics, including, but not limited to, topical anesthetics, injected anesthetics, and any other suitable means of inducing anesthesia. Issues connected with the use of anesthesia in the oral cavity are discussed in the following references: Frank U, et al., "Vascular and cellular responses of teeth after localized controlled cooling," Cryobiology, 1972 December, 9(6):526–33; Hutchings M L, "Nerve Damage and nerve blocks," J. Am. Dent. Assoc., 1996 January; 127(1):25, Ellis S, "Sedation in general practice," Br. Dent. J., Feb. 10, 1996. 180(3):88; Nist R A, et al., "An evaluation of the incisive nerve block and combination inferior alveolar and incisive nerve blocks in mandibular anesthesia," J. Endod., 1992 September, 18(9):455–9; Meier E, "Anesthesia problems in dentistry," Schweiz Monatsschr. Zabrimed., 1993, 103(2):205–7, 232–4; Jofre J, et al., "Design and preliminary evaluation of an extraoral Gow-Gates guiding device," Oral Surg. Oral Med. Oral Pathol. Oral Radiol. Endod., 1998 June, 85(6):661–4; Martof A B, "Anesthesia of the teeth, supporting structures, and oral mucous membrane," Otolaryngol. Clin. North Am., 1981 August, 14(3):653–68; Weathers A, "Taking the mystery out of endodontics, Part 6. Painless anesthesia for the "hot" tooth," Dent. Today, 1999 December, 18(12):90–3; Meechan J G, "How to overcome failed local anaesthesia," Br. Dent. J., Jan. 9, 1999, 186(1):15–20; Lepere A J, "Maxillary nerve block via the greater palatine canal: new look at an old technique," Anesth. Pain Control Dent., 1993 Fall, 2(4):195–7; Noisser H O, et al., "Management of chronic pain conditions—anesthesiologic aspects," Chirurg., 1983 December, 54(12):785–8; Henthorn R W, et al., "A reliable method of testing regional block," Reg. Anesth., 1993 March–April, 18(2):139; Davies M W, et al., "Anaesthetic techniques for chair dental anaesthesia," Anaesthesia, 1995

October, 59(10):922–3; Quinn J H, "Inferior alveolar nerve block using the internal oblique ridge," J. Am. Dent. Assoc., 1998 August, 129(8):1147–8; Gomolka K A, "The AMSA block: local anesthesia without collateral numbness," CDS Rev., 2000 October, 93(7):34; Franklin L K, "Electronic dental anesthesia: an injection-free alternative—a review," Pract. Periodontics Aesthet. Dent., 1997 January–February, 9(1 ):103–4, 106; Dhanji A R, "Overcoming failed local anaesthesia," Br. Dent. J., Apr. 10, 1999, 186(7):316–7; Thomas J A, "Anesthetizing the dental pulp," Endod. Rep. 1992, 7(2):6–8; Young E R, et al., "Successful mandibular anesthesia following numerous unsuccessful attempts: a case report," J. Can. Dent. Assoc., 1993 October, 59(10):845–50; Hannington-Kiff J G, "Cryoanalgesia for postoperative pain," Lancet, Apr. 12, 1980, 1(8172):829; Carpentier P, Rev. Odontostomatol. (Paris), 1985 November–December, 14(6):453–8, (French); DeWitt K, "What . . . another injection technique," J. Wis. Dent. Assoc., 1984 January, 60(1):22–3; Hawkins P L, "The second divisions block: an easy cure for the "difficult to numb" patient," GMDA Bull., 1987 March, 54(3):91–2; Gaillard M M, et al., "New techniques of loco-regional anesthesia. What are they worth" Inf. Dent., Nov. 10, 1988, 70(39):3901–6; Hogarth D L, "Maxillary nerve block anaesthesia," Aust. Dent. J., 1991 August, 36(4):326; Durick R J, "The third and second divisions of the trigeminal nerve: dental considerations," J. Tenn. Dent. Assoc., 1995 April, 75(2):18–22.

The preferred embodiments have been described in connection with specific embodiments thereof. It will be understood that it is capable of further modification, and this application is intended to cover any variations, uses, or adaptations of the invention following, in general, the principles of the invention and including such departures from the present disclosure as come within known or customary practices in the art to which the invention pertains and as may be applied to the essential features hereinbefore set forth, and as fall within the scope of the invention and any equivalents thereof. Each reference cited herein, including but not limited to patents and technical literature, is hereby incorporated by reference in its entirety.

What is claimed is:

1. An apparatus for applying heat or cold to a patient's oral tissue, the apparatus comprising an upper member substantially conforming to a contour of an upper gum line, a lower member substantially conforming to a contour of a lower gum line, a first hinge member configured to provide a compressive force, and a second hinge member configured to provide a compressive force, wherein the first hinge member joins a first end of the upper member to a first end of the lower member, wherein the second hinge member joins a second end of the upper member to a second end of the lower member, wherein the apparatus comprises a material configured to deliver heat or cold to the patient's oral tissue, and wherein when the apparatus is inserted into a patient's mouth, the compressive force maintains the upper member substantially in contact with an upper gum and the lower member substantially in contact with a lower gum over a range of relative motion of the upper gum and lower gum.

2. An apparatus for applying heat or cold to a patient's oral tissue, the apparatus comprising an upper member substantially conforming to a contour of an upper gum line, a lower member substantially conforming to a contour of a lower gum line, a first hinge member, and a second hinge member, wherein at least one hinge member is configured to provide a compressive force, wherein the apparatus comprises a material configured to deliver heat or cold to the patient's oral tissue.

3. That apparatus of claim 2, wherein at least one of said members comprises an impermeable polymeric material encapsulating a heat transfer material.

4. That apparatus of claim 2, wherein the upper member comprises an impermeable polymeric material encapsulating a heat transfer material.

5. That apparatus of claim 2, wherein the lower member comprises an impermeable polymeric material encapsulating a heat transfer material.

6. That apparatus of claim 2, wherein the upper member and the lower member comprise an impermeable polymeric material encapsulating a heat transfer material.

7. The apparatus of claim 3, wherein the heat transfer material comprises a gel or a liquid.

8. The apparatus of claim 2, wherein a member selected from the group consisting of the upper member, the lower member, the first hinge member, and the second hinge member comprises a solid polymeric material, the material having a high heat capacity.

9. The apparatus of claim 2, wherein a member selected from the group consisting of the upper member, the lower member, the first hinge member, and the second a hinge member comprises a sponge.

10. The apparatus of claim 9, wherein the sponge comprises a polymeric material selected from the group consisting of chloroprene rubber, neoprene, styrene butadiene rubber, acrylonitrile butadiene rubber, ethylene propylene diene methylene, polyvinylchloride, polyethylene, and combinations thereof.

11. The apparatus of claim 9, wherein the sponge comprises a closed cell sponge.

12. The apparatus of claim 9, wherein the sponge comprises an open cell sponge.

13. The apparatus of claim 2, comprising a biocompatible material.

14. The apparatus of claim 2, comprising a polymeric material.

15. The apparatus of claim 14, wherein the polymeric material is pliable.

16. The apparatus of claim 15, wherein the polymeric material is selected from the group consisting of polyethylene, nylon, polyethylethylketone, polyethylene terephthalate, polyether block amide copolymer, polymethylmethacrylate, polytetrafluoroethylene, polyurethane, polyvinylchloride, polydimethylsiloxane, styrenic copolymer, and combinations thereof.

17. An apparatus for applying heat or cold to a patient's oral tissue, the apparatus comprising an upper member substantially conforming to a contour of an upper gum line hinged to a lower member substantially conforming to a contour of a lower gum line so that rotation of said upper member towards said lower member about said hinge provides a compression force between said upper and lower member.

18. A method of treating a patient suffering from pain associated with an oral tissue, the method comprising the steps of:

providing an apparatus comprising an upper member substantially conforming to a contour of an upper gum, a lower member substantially conforming to a contour of a lower gum, a first hinge member, and a second hinge member, wherein the first hinge member joins a first end of the upper member to a first end of the lower member, wherein the second hinge member joins a second end of the upper member to a second end of the lower member;

cooling the apparatus to a temperature of between about 4° C. and about 15° C.;

inserting the apparatus into an oral cavity; and positioning the apparatus such that a compressive force is exerted by the first hinge member and the second hinge member such that the upper member is substantially maintained in contact with the upper gum and the lower member is substantially maintained in contact with the lower gum over a range of relative motion of the upper gum and lower gum, whereby cold is delivered to the oral tissue such that pain is reduced.

19. A method of treating a patient suffering from pain associated with an oral tissue, the method comprising the steps of:

inserting into the oral cavity a device comprising an upper member substantially conforming to a contour of an upper gum line, a lower member substantially conforming to a contour of a lower gum line, a first hinge member, and a second hinge member, wherein at least one hinge member is configured to exert a compressive force to maintain the upper member substantially in contact with an upper gum and the lower member substantially in contact with a lower gum, and wherein at least one of the members has a temperature of between about 4° C. and about 15° C.; and transferring heat from a portion of the oral tissue to a portion of the device, whereby cryoanesthesia is delivered to the oral tissue.

20. A method of treating a patient suffering from pain associated with an oral tissue, the method comprising the steps of:

inserting into the oral cavity a device comprising an upper member substantially conforming to a contour of an upper gum line hinged to a lower member substantially conforming to a contour of a lower gum line;

rotating said upper member and said lower member about said hinge during said insertion into the oral cavity to exert a compressive force to maintain the upper member substantially in contact with an upper gum and the lower member substantially in contact with a lower gum; and transferring heat from a portion of the oral tissue to a portion of the device, whereby cryoanesthesia is delivered to the oral tissue.

\* \* \* \* \*